United States Patent

Buerger et al.

[11] Patent Number: 6,114,335
[45] Date of Patent: Sep. 5, 2000

[54] BENZOYLGUANIDINE DERIVATIVES, PROCESS FOR THEIR PREPARATION THEIR USE IN THE PREPARATION OF MEDICINES

[75] Inventors: Erich Buerger, Bingen; Christian Eickmeier, Wiesbaden; Otto Roos, Schwabenheim, all of Germany

[73] Assignee: Boehringer Ingelheim KG, Ingelheim, Germany

[21] Appl. No.: 09/101,792

[22] PCT Filed: Jan. 16, 1997

[86] PCT No.: PCT/EP97/00177

§ 371 Date: Sep. 25, 1998

§ 102(e) Date: Sep. 25, 1998

[87] PCT Pub. No.: WO97/26253

PCT Pub. Date: Jul. 24, 1997

[30] Foreign Application Priority Data

Jan. 16, 1996 [DE] Germany .................. 196 01 303

[51] Int. Cl.[7] .................. A61K 31/496; C07D 403/10; C07D 405/10; C07D 409/10
[52] U.S. Cl. .................. 514/252.13; 514/253.01; 514/254.01; 514/255.01; 544/365; 544/372; 544/374; 544/379; 544/393
[58] Field of Search .................. 544/379, 393, 544/372, 365, 374; 514/252, 255

[56] References Cited

U.S. PATENT DOCUMENTS 5,753,680  5/1998  Gericke et al. .................. 514/331
5,783,576  7/1998  Roos et al. .................. 514/242

FOREIGN PATENT DOCUMENTS

| 0589336 | 3/1994 | European Pat. Off. . |
| 0600371 | 6/1994 | European Pat. Off. . |
| 0602522 | 6/1994 | European Pat. Off. . |
| 0667341 | 8/1995 | European Pat. Off. . |
| 4337611 | 5/1995 | Germany . |
| 95/12584 | 5/1995 | WIPO . |

OTHER PUBLICATIONS

*Medicinal Chemistry* (3rd Ed.) by Alfred Burger, p. 72–77, 1970.

Primary Examiner—Emily Bernhardt
Attorney, Agent, or Firm—R. P. Raymond; M-E M. Devlin, Esq.; A. R. Stempel, Esq.

[57] ABSTRACT

The present invention relates to novel benzoylguanidine derivatives, processes for preparing them and their use in the preparation of pharmaceutical compositions.

The novel benzoylguanidine derivatives correspond to general formula (I)

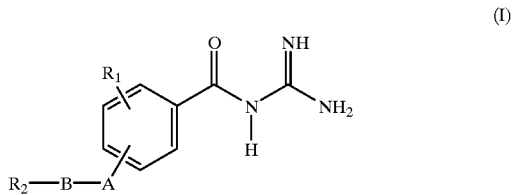

which benzoylguanidine derivatives are useful in the treatment of ischemia.

9 Claims, No Drawings

BENZOYLGUANIDINE DERIVATIVES, PROCESS FOR THEIR PREPARATION THEIR USE IN THE PREPARATION OF MEDICINES

The present invention relates to novel benzoylguanidine derivatives, processes for preparing them and their use in the preparation of pharmaceutical compositions.

The novel benzoylguanidine derivatives correspond to the general formula (I)

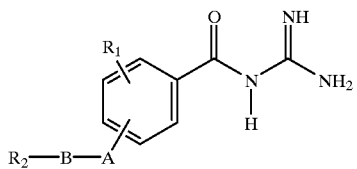

wherein $R_1$ denotes $R_3$—$SO_2$— or $R_3$—NH—$SO_2$—, F, Cl or $CF_3$;

A denotes one of the divalent groups which is bonded to the benzoylguanidine system via a nitrogen atom:

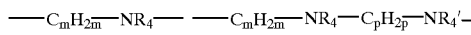

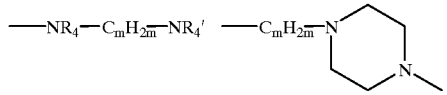

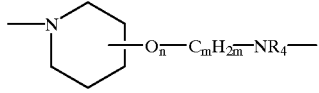

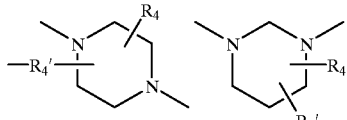

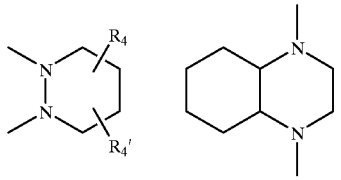

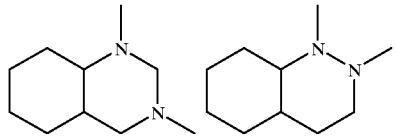

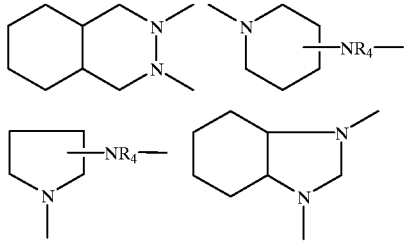

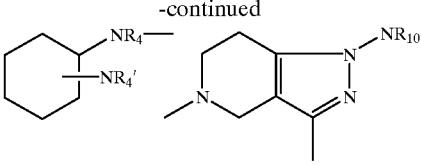

and m represents 0, 1, 2, 3, 4, 5 or 6
n represents 0 or 1
represents 0, 1, 2, 3 or 4;

B denotes one or more of the following groups in any order (—$CH_2$—)$_a$, (—CHOH—)$_b$, (—CO—)$_c$, (—CS—)$_d$ and/or (—$NR_{11}$—) and a represents from 0 to 8, preferably 1, 2, 3 or 4,
b represents 0, 1 or 2, preferably 1,
c represents 0, 1 or 2, preferably 1,
d represents 0, 1 or 2, preferably 1;

$R_2$ denotes unsubstituted or substituted $C_{1-8}$-alkyl, unsubstituted or substituted aryl, —$NR_5R_6$ or a preferably 5- or 6-membered heterocyclic group

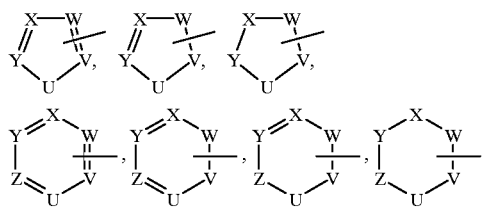

which may optionally be ring-condensed with one or two phenyl systems and wherein U, V, W, X, Y and optionally Z, which may be the same or different, denote:

$CH_2$, CH, CO, $NR_7$, N, O or S, any of these bearing hydrogen, or $R_7$ when this represents hydrogen, being optionally substituted by B;

$R_3$ denotes $C_{1-8}$-alkyl, halogen- or phenyl-substituted $C_{1-8}$-alkyl, wherein the phenyl group may contain up to three substituents selected from the group comprising halogen, $C_{1-4}$-alkyl or $C_{1-4}$-alkoxy, $R_4$ and $R_4'$, which may be identical or different, denote hydrogen, $C_{1-4}$-alkyl $R_4$ and $R_4'$ may also denote phenyl, benzyl and $C_{3-7}$-cycloalkyl;

$R_5$ denotes hydrogen or $C_{1-8}$-alkyl, aryl, aralkyl;

$R_6$ denotes hydrogen or $C_{1-8}$-alkyl, aryl, aralkyl;

$R_7$ denotes hydrogen, $C_{1-4}$-alkyl, aryl or aralkyl.

Preferred compounds of general formula I are those wherein $R_1$ denotes $R_3$—$SO_2$— or $R_3$—NH—$SO_2$—;

A denotes one of the divalent groups which is bonded to the benzoylguanidine system via a nitrogen atom

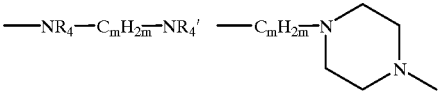

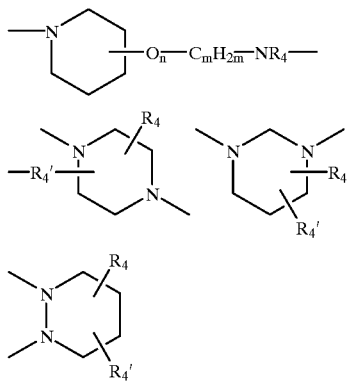

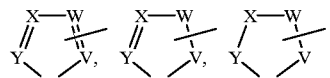

m is an integer 0, 1, 2, 3, 4, 5 or 6
n is an integer 0 or 1
p is an integer 0, 1, 2, 3 or 4;
B denotes one or more of the following groups in any order (—CH$_2$—)$_a$, (—CHOH—)$_b$, (—CO—)$_c$, (—CS—)$_d$ and/or (—NR$_{11}$—) and
a represents an integer from 0 to 4,
b represents 0 or the integer 1,
c represents 0 or the integer 1,
d represents 0 or the integer 1,
R$_2$ denotes substituted or unsubstituted C$_{1-4}$-alkyl, substituted or unsubstituted aryl, —NR$_5$R$_6$ or a 5- or 6-membered heterocyclic group

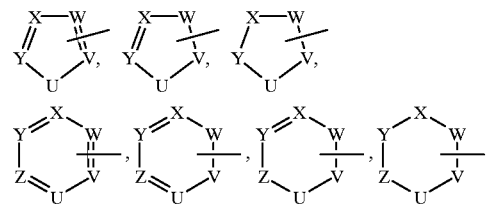

which may optionally be ring-condensed by one or two phenyl systems and wherein U, V, W, X, Y and optionally Z, which may be the same or different, denote:
CH$_2$, CH, CO, NR$_7$, N, O or S, any of these bearing hydrogen, or R$_7$ when this represents hydrogen, being optionally substituted by B;
R$_3$ denotes C$_{1-4}$-alkyl;
R$_4$ and R$_4$', which may be identical or different, denote hydrogen, C$_{1-4}$-alkyl R$_4$ and R$_4$' may also denote phenyl, benzyl and C$_{3-7}$-cycloalkyl;
R$_5$ denotes hydrogen or C$_{1-4}$-alkyl, aryl, aralkyl;
R$_6$ denotes hydrogen or C$_{1-4}$-alkyl, aryl, aralkyl;
R$_7$ denotes C$_{1-4}$-alkyl, aryl or aralkyl.
Particularly preferred compounds of formula I are those wherein
R$_1$ denotes CH$_3$—SO$_2$—;
A denotes

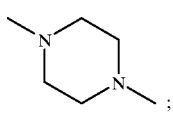

B denotes one or more of the following groups in any desired sequence (—CH$_2$—)$_a$, (—CHOH—)$_b$, (—CO—)$_c$, (—CS—)$_d$ and/or (—NR$_{11}$—) and
a represents an integer from 0 to 4,
b represents 0 or the integer 1,
c represents 0 or the integer 1,
d represents 0 or the integer 1,
R$_2$ denotes a 5-membered heterocyclic group which may optionally be ring-condensed by one or two phenyl systems and wherein U, V, W, X, Y and optionally Z, which may be the same or different, denote:
CH$_2$, CH, NR$_7$, N, O or S, any of these bearing hydrogen, or R$_7$ when this represents hydrogen, being optionally substituted by B and only one heteroatom is present in the ring system;
R$_3$ denotes C$_{1-4}$-alkyl;
R$_4$ and R$_4$', which may be identical or different, denote hydrogen, C$_{1-4}$-alkyl;
R$_5$ denotes hydrogen or C$_{1-4}$-alkyl, aryl, aralkyl;
R$_6$ denotes hydrogen or C$_{1-4}$-alkyl, aryl or aralkyl;
R$_7$ denotes hydrogen, C$_{1-4}$-alkyl, aryl or aralkyl.
Unless specifically stated otherwise, the general definitions are used in the following way:
C$_{1-4}$-alkyl and C$_{1-8}$-alkyl generally represent a branched or unbranched hydrocarbon group having 1 to 4 or 8 carbon atom(s) which may optionally be substituted by one or more halogen atoms, preferably fluorine, and these substituents may be identical to one another or different from one another. The following hydrocarbon groups are mentioned by way of example:
methyl, ethyl, propyl, 1-methylethyl (isopropyl), n-butyl, 1-methylpropyl, 2-methylpropyl, 1,1-dimethyl-ethyl, pentyl, 1-methylbutyl, 2-methylbutyl, 3-methyl-butyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Unless otherwise specified, lower alkyl groups having 1 to 4 carbon atoms such as methyl, ethyl, propyl, isopropyl, n-butyl, 1-methylpropyl, 2-methylpropyl or 1,1-dimethylethyl are preferred.
Alkoxy generally represents a straight-chained or branched hydrocarbon group having 1 to 8 carbon atoms which is bound via an oxygen atom. A lower alkoxy group having 1 to 4 carbon atoms is preferred. The methoxy group is particularly preferred.
Aryl generally represents an aromatic group having 6 to 10 carbon atoms, including those in compositions in which the aromatic group may be substituted by one or more lower alkyl groups, trifluoromethyl groups, cyano groups, alkoxy groups, nitro groups, amino groups and/or one or more halogen atoms, either identical or different; the preferred aryl group is an optionally substituted phenyl group, the preferred substituents being halogen (such as fluorine, chlorine or bromine), cyano and hydroxyl.
Aralkyl generally denotes an aryl group having 7 to 14 carbon atoms bound via an alkylene chain, the aromatic group optionally being substituted by one or more lower alkyl groups, alkoxy groups, nitro groups, amino groups and/or one or more halogen atoms, either identical or different. Aralkyl groups having 1 to 6 carbon atoms in the aliphatic part and 6 carbon atoms in the aromatic part are preferred.

Unless otherwise stated, the preferred aralkyl groups are benzyl, phenethyl and phenylpropyl.

Halogen denotes fluorine, chlorine, bromine and iodine, preferably chlorine and bromine.

Unless otherwise stated, amino denotes an $NH_2$ functional group which may optionally be substituted by one or two $C_{1-8}$-alkyl, aryl or aralkyl groups, either identical or different.

Alkylamino denotes, for example, methylamino, ethylamino, propylamino, 1-methylenethylamino, butylamino, 1-methylpropylamino, 2-methylpropylamino or 1,1-dimethylethylamino.

Dialkylamino denotes, for example, dimethylamino, diethylamino, dipropylamino, dibutylamino, di-(1-methylethyl)amino, di-(1-methylpropyl)amino, di-2-methylpropylamino, ethylmethylamino, methylpropylamino.

Cycloalkyl generally denotes a saturated or unsaturated cyclic hydrocarbon group having 5 to 9 carbon atoms which may optionally be substituted by one or more halogen atoms, preferably fluorine, which may be identical or different. Cyclic hydrocarbon groups having 3 to 6 carbon atoms are preferred. Examples include cyclopropyl, cyclobutyl, cyclopentyl, cyclopentenyl, cyclohexyl, cyclohexenyl, cycloheptyl, cycloheptenyl, cycloheptadienyl, cyclooctyl, cyclooctenyl, cyclooctadienyl and cyclononinyl.

Heteroaryl, within the scope of the above definition, generally denotes a 5- to 6-membered ring which may contain oxygen, sulphur and/or nitrogen as heteroatoms and onto which another aromatic ring may be fused. 5-and 6-membered aromatic rings which contain an oxygen, a sulphur and/or up to two nitrogen atoms and which are optionally benzocondensed are preferred.

Examples of particular heterocyclic systems are as follows: acridinyl, acridonyl, alkylpyridinyl, anthraquinonyl, ascorbyl, azaazulenyl, azabenzanthracenyl, azabenzanthrenyl, azachrysenyl, azacyclazinyl, azaindolyl, azanaphthacenyl, azanaphthalenyl, azaprenyl, azatriphenylenyl, azepinyl, azinoindolyl, azinopyrrolyl, benzacridinyl, benzazapinyl, benzofuryl, benzonaphthyridinyl, benzopyranonyl, benzopyranyl, benzopyronyl, benzoquinolinyl, benzoquinolizinyl, benzothiepinyl, benzothiophenyl, benzylisoquinolinyl, bipyridinyl, butyrolactonyl, caprolactamyl, carbazolyl, carbolinyl, catechinyl, chromenopyronyl, chromonopyranyl, cumarinyl, cumaronyl, decahydroquinolinyl, decahydroquinolonyl, diazaanthracenyl, diazaphenanthrenyl, dibenzazapinyl, dibenzofuranyl, dibenzothiphenyl, dichromylenyl, dihydrofuranyl, dihydroisocumarinyl, dihydroisoquinolinyl, dihydropyranyl, dihydropyridinyl, dihydropyridonyl, dihydropyronyl, dihydrothiopyranyl, diprylenyl, dioxanthylenyl, oenantholactamyl, flavanyl, flavonyl, fluoranyl, fluoresceinyl, furandionyl, furanochromanyl, furanonyl, furanoquinolinyl, furanyl, furopyranyl, furopyronyl, heteroazulenyl, hexahydropyrazinoisoquinolinyl, hydrofuranyl, hydrofuranonyl, hydroindolyl, hydropyranyl, hydropyridinyl, hydropyrrolyl, hydroquinolinyl, hydrothiochromenyl, hydrothiophenyl, indolizidinyl, indolizinyl, indolonyl, isatinyl, isatogenyl, isobenzofurandionyl, isobenzfuranyl, isochromanyl, isoflavonyl, isoindolinyl, isoindolobenzazapinyl, isoindolyl, isoquinolinyl, isoquinuclidinyl, lactamyl, lactonyl, maleimidyl, monoazabenzonaphthenyl, naphthalenyl, naphthimidazopyridinedionyl, naphthindolizinedionyl, naphthodihydropyranyl, naphthofuranyl, naphthyridinyl, oxepinyl, oxindolyl, oxolenyl, perhydroazolopyridinyl, perhydroindolyl, phenanthraquinonyl, phthalideisoquinolinyl, phthalimidyl, phthalonyl, piperidinyl, piperidonyl, prolinyl, parazinyl, pyranoazinyl, pyranoazolyl, pyranopyrandionyl, pyranopyridinyl, pyranoquinolinyl, pyranopyrazinyl, pyranyl, pyrazolopyridinyl, pyridinethionyl, pyridinonaphthalenyl, pyridinopyridinyl, pyridinyl, pyridocolinyl, pyridoindolyl, pyridopyridinyl, pyridopyrimidinyl, pyridopyrrolyl, pyridoquinolinyl, pyronyl, pyrrocolinyl, pyrrolidinyl, pyrrolizidinyl, pyrrolizinyl, pyrrolodioazinyl, pyrrolonyl, pyrrolopyrmidinyl, pyrroloquinolonyl, pyrrolyl, quinacridonyl, quinolinyl, quinolizidinyl, quinolizinyl, quinolonyl, quinuclidinyl, rhodaminyl, spirocumaranyl, succinimidyl, sulpholanyl, sulpholenyl, tetrahydrofuranyl, tetrahydroisoquinolinyl, tetrahydropyranyl, tetrahydropyridinyl, tetrahydrothiapyranyl, tetrahydrothiophenyl, tetrahydrothipyranonyl, tetrahydrothipyranyl, tetronyl, thiaphenyl, thiachromanyl, thiadecalinyl, thianaphthenyl, thiapyranyl, thiapyronyl, thiazolopyridinyl, thienopyridinyl, thienopyrrolyl, thienothiophenyl, thiepinyl, thiochromenyl, thiocumarinyl, thiopyranyl, triazaanthracenyl, triazinoindolyl, triazolopyridinyl, tropanyl, xanthenyl, xanthonyl, xanthydrolyl, adeninyl, alloxanyl, alloxazinyl, anthranilyl, azabenzanthrenyl, azabenzonaphthenyl, azanaphthacenyl, azaphenoxazinyl, azapurinyl, azinyl, azoloazinyl, azolyl, barbituric acid, benzazinyl, benzimidazolethionyl, benzimidazolonyl, benzisothiazolyl, benzisoxazolyl, benzocinnolinyl, benzodiazocinyl, benzodioxolanyl, benzodioxolyl, benzopyridazinyl, benzothiazepinyl, benzothiazinyl, benzothiazolyl, benzoxazinyl, benzoxazolinonyl, benzoxazolyl, cinnolinyl, depsidinyl, diazaphenanthrenyl, diazepinyl, diazinyl, dibenzoxazepinyl, dihydrobenzimidazolyl, dihydrobenzothiazinyl, dihydrooxazolyl, dihydropyridazinyl, dihydropyrimidinyl, dihydrothiazinyl, dioxanyl, dioxenyl, dioxepinyl, dioxinonyl, dioxolanyl, dioxolonyl, dioxopiperazinyl, dipyrimidopyrazinyl, dithiolanyl, dithiolenyl, dithiolyl, flavinyl, furopyrimidinyl, glycocyamidinyl, guaninyl, hexahydropyrazinoisoquinolinyl, hexahydropyridazinyl, hydantoinyl, hydroimidazolyl, hydroparazinyl, hydropyrazolyl, hydropyridazinyl, hydropyrimidinyl, imidazolinyl, imidazolyl, imidazoquinazolinyl, imidazothiazolyl, indazolebenzopyrazolyl, indoxazenyl, inosinyl, isoalloxazinyl, isothiazolyl, isoxazolidinyl, isoxazolinonyl, isoxazolinyl, isoxazolonyl, isoxazolyl, lumazinyl, methylthyminyl, methyluracilyl, morpholinyl, naphthimidazolyl, oroticyl, oxathianyl, oxathiolanyl, oxazinonyl, oxazolidinonyl, oxazolidinyl, oxazolidonyl, oxazolinonyl, oxazolinyl, oxazolonyl, oxazolopyrimidinyl, oxazolyl, perhydrocinnolinyl, perhydropyrroloazinyl, perhydropyrrolothiazinyl, perhydrothiazinonyl, perimidinyl, phenazinyl, phenothiazinyl, phenoxathiinyl, phenoxazinyl, phenoxazonyl, phthalazinyl, piperazindionyl, piperazinodionyl, polyquinoxalinyl, pteridinyl, pterinyl, purinyl, pyrazinyl, pyrazolidinyl, pyrazolidonyl, pyrazolinonyl, parazolinyl, pyrazolobenzodiazepinyl, pyrazolonyl, pyrazolopyrimidinyl, pyrazolotriazinyl, pyrazolyl, pyridazinyl, pyridazonyl, pyridopyrazinyl, pyridopyrimidinyl, pyrimidinethionyl, pyrimidinyl, pyrimidionyl, pyrimidoazepinyl, pyrimidopteridinyl, pyrrolobenzodiazepinyl, pyrrolodiazinyl, pyrrolopyrimidinyl, quinazolidinyl, quinazolinonyl, quinazolinyl, quinoxalinyl, sultamyl, sultinyl, sultonyl, tetrahydrooxazolyl, tetrahydropyrazinyl, tetrahydropyridazinyl, tetrahydroquinoxalinyl, tetrahydrothiazolyl, thiazepinyl, thiazinyl, thiazolidinonyl, thiazolidinyl, thiazolinonyl, thiazolinyl, thiazolobenzimidazolyl, thiazolyl, thienopyrimidinyl, thiazolidinonyl, thyminyl, triazolopyrimidinyl, uracilyl, xanthinyl, xylitolyl, azabenzonapththenyl, benzofuroxanyl, benzothiadiazinyl, benzotriazepinonyl, benzotriazolyl, benzoxadiazinyl, dioxadiazinyl, dithiadazolyl, dithiazolyl, furazanyl, furoxanyl, hydrotriazolyl, hydroxytrizinyl, oxadiazinyl, oxadiazolyl, oxathiazinonyl, oxatriazolyl, pentazinyl, pentazolyl, petrazinyl, polyoxadiazolyl, sydonyl, tetraoxanyl, tetrazepinyl, tetrazinyl, tetrazolyl, thiadiazinyl, thiadiazolinyl, thiadiazolyl, thiadioxazinyl, thiatriazinyl, thiatriazolyl, triazepinyl, triazinoindolyl, triazinyl, triazolinedionyl, triazolinyl, triazolyl, trioxanyl, triphenodioxazinyl, triphenodithiazinyl, trithiadiazepinyl, trithianyl or trioxolanyl.

As a result of their effect as inhibitors of cellular $Na^+/H^+$ exchange, the compounds of general formula I may be used as active substances in pharmaceutical compositions or they may be used as intermediates in the preparation of such active substances. The compounds according to the invention are effective against arrhythmias which occur, for example, in hypoxia. They can also be used in diseases connected with ischaemia (such as cardial, cerebral, gastrointestinal, pulmonary and renal ischaemia, ischaemia of the liver and ischaemia of the skeletal musculature). Such diseases include, for example, coronary heart disease, angina pectoris, pulmonary embolism, acute or chronic kidney failure, chronic kidney insufficiency, cerebral infarct, reperfusion damage caused by the return of blood supply to areas of the brain after the dissolving of vascular occlusions and acute and chronic circulatory disorders of the brain. Here, the compounds mentioned may also be used in conjunction with thrombolic agents such as t-PA, streptokinase and urokinase.

During reperfusion of the ischaemic heart (e.g. after an attack of angina pectoris or cardiac infarct) irreversible damage may be caused to cardiomyocytes in the affected region. The compounds according to the invention have a cardioprotective activity, inter alia, in such cases.

The treatment of ischaemia also includes the prevention of damage to transplants (e.g. as protection for the transplant before, during and after transplanting and during the storage of transplanted organs) which may occur in connection with transplants. The compounds are also drugs with a protective effect during angioplastic surgical interventions on the heart and peripheral blood vessels.

In essential hypertonia and diabetic nepthropathy, the cellular exchange of sodium protons is increased. The compounds mentioned above are therefore suitable as inhibitors of this exchange as a preventive treatment for these diseases.

The compounds according to the invention are also characterised by their powerful inhibitory effect on the proliferation of cells. Consequently, the compounds are valuable drugs in diseases in which cell proliferation plays a primary or secondary part and can be used as agents against cancers, atherosclerosis, organ hypotrophias and hyperplasias, fibrotic diseases and late complications of diabetes.

Pharmacological Data
Inhibition of the $Na^+/H^+$ Exchanger in Human Intestinal Cancer Cells (HT-29):

HT-29 cells were incubated in growth medium at 37° C., 5% $CO_2$. After 3–5 days the growth medium was removed, the cells were washed and charged with 7.5 μM BCECF-AM (pH-sensitive fluorescent dye) at 37° C. without any $CO_2$. After 30 minutes the cells were washed and acidified with the following medium: 70 mM choline chloride, 20 mM $NH_4Cl$, mM $MgCl_2$, 1.8 mM $CaC_2$, 5 mM glucose and 15 mM HEPES, pH 7.5.

After 6 minutes incubation at 37° C. without $CO_2$, the cells were washed and incubated for 5 minutes with washing medium: 120 mM choline chloride, 5 mM KCl, 1 mM $MgCl_2$, 1.8 mM $CaCl_2$, 5 mM glucose and 15 mM MOPS, pH 7.0. The washing medium was removed and control medium was added with or without the test compound: 120 mM NaCl, 5 mM KCl, 1 mM $MgCl_2$, 1.8 mM $CaCl_2$, 5 mM glucose, 15 mM MOPS, pH 7.0.

The cells were incubated for 4 minutes at 37° C. without $CO_2$ and measured by fluorimetry (CytoFluor 2350). The fluorescence of the dye BCECF was measured at the excitation wavelengths of 485 nm (pH sensitive) and 440 nm (non pH-sensitive) and at the emission wavelength of 530 nm. The cytoplasmic pH was calculated from the ratio of fluorescences at 485 and 440 nm. The fluorescence ratio was calibrated by measuring the fluorescence signal after equilibration of external and internal pH with nigericin.

| Example | $IC_{50}/10^{-6}$ mol $1^{-1}$ |
|---------|-------------------------------|
| 1 | 0.500 |
| 3 | 0.029 |
| 4 | 0.031 |

The active substances according to general formula I may be used as an aqueous injectable solution (e.g. for intravenous, intramuscular or subcutaneous administration), in the form of a tablet, suppository, ointment, as a plaster for transdermal administration, as an aerosol for inhalation into the lungs or as a nasal spray.

The content of active substance in a tablet or suppository is between 5 and 200 mg, preferably between 10 and 50 mg. For inhalation the single dose is between 0.05 and 20 mg, preferably between 0.2 and 5 mg. For parenteral injection the single dose is between 0.1 and 50 mg, preferably between 0.5 and 20 mg. If necessary, these doses may be given several times a day.

The following are Examples of pharmaceutical preparations containing the active substance:

| Tablets | |
|---|---|
| Active substance according to general formula I | 20.0 mg |
| Magnesium stearate | 1.0 mg |
| Corn starch | 62.0 mg |
| Lactose | 83.0 mg |
| Polyvinylpyrrolidone | 1.6 mg |

| Solution for injection | |
|---|---|
| Active substance according to general formula I | 0.3 g |
| Sodium chloride | 0.9 g |
| Water for injections made up to | 100 ml |

The solution can be sterilised using standard methods.

| Aqueous solution for nasal inhalation | |
|---|---|
| Active substance according to general formula I | 0.3 g |
| Sodium chloride | 0.9 g |
| Benzalkonium chloride | 0.01 mg |
| Purified water made up to | 100 ml |

The solution describe d above is suitable for nasal administration in a spray or in conjunction with a device which produces an aerosol having a particle size preferably between 2 and 6 μm for administration into the lungs.

Capsules for Inhalation

The compounds of general formula 1 are prepared in micronised form (particle size, in the main, being between 2 and 6 μM), optionally with the addition of micronised carrier substances such as lactose, and packed into hard gelatine capsules. They may be inhaled using conventional devices for powder inhalation. Each capsule contains, for example, between 0.2 and 20 mg of the active substance of general formula I and 0 to 40 mg of lactose.

| Aerosol for inhalation | |
|---|---|
| Active substance according to general formula I | 1 part |
| Soya lecithin | 0.2 parts |
| Propellant gas mixture made up to | 100 parts |

The preparation is preferably packed into aerosol containers with a metering valve and the individual amount released each time is designed to deliver a dose of 0.5 mg. For the other doses in the range specified, preparations with a higher or lower content of active substance are preferably used.

| Ointment (composition in g/100 g of ointment) | |
|---|---|
| Active substance according to general formula I | 2 g |
| Fuming hydrochloric acid | 0.011 g |
| Sodium pyrosulphite | 0.05 g |
| Mixture of equal parts of cetylalcohol and stearylalcohol | 20 g |
| White vaseline | 5 g |
| Artificial bergamot oil | 0.075 g |
| Distilled water made up to | 100 |

The ingredients are mixed together in the usual way to form an ointment.

The general procedure for preparing benzoylguanidines of general formula I (I)

from the corresponding benzoic acid derivatives, consists in nucleophilically substituting a benzoic acid derivative of general formula II, (II)

(wherein P denotes a nucleofugic leaving group), with the desired substituent from the compound of general formula III, $$R_2BAQ \qquad (III)$$

wherein Q is a leaving group which may be substituted by an electrophile,
and the resulting benzoic acid derivative of general formula IV (IV)

is suspended in a suitable, preferably anhydrous, solvent—preferably dimethylformamide—and mixed with N-methylmorpholine and carbonyldiimidazole (CDI) and combined with a mixture of a solution or suspension of a base, preferably dimethylformamide, with a guanidine salt, preferably guanidine hydrochloride.

The activeated acid derivatives can be prepared directly, in a manner known per se, from the basic benzoic acid derivatives of general formula IV (IV)

A number of suitable methods of preparing activated carboxylic acid derivatives based on benzoic acid derivatives of general formula IV are given with the source literature in J. March, Advanced Organic Chemistry, Third Edition (John Wiley & Sons, 1985), page 350.

Reaction of an activated carboxylic acid derivative with a guanidine salt is carried out in a manner known per se in a protic or aprotic polar but inert organic solvent.

Some of the basic benzoic acid derivatives of formula IV are known and are described in the literature. The hitherto unknown compounds of formula IV may be prepared using methods known from the literature.

The corresponding benzoic acids are obtained, for example, by reacting the correspondingly substituted piperazines with 4-chloro-3-methylsulphonylbenzoic acid, wherein nucleophilic substitution takes place in the 4-position. In order to do this, 10 mM of 4-chloro-3-methylsulphonylbenzoic acid and 50 mM piperazine are heated to 120° C. for 4 hours under an inert gas. Crystallisation from methanol yields the correspondingly substituted benzoic acids.

10 mM of the corresponding benzoic acid derivative is suspended in 40 ml of anhydrous DMF and mixed with 10 mM of N-methylmorpholine. 13 mM of carbonyldiimidazole (CDI) are added to the solution obtained and this is stirred for 2 hours at ambient temperature. In a second mixture, 14 mM NaH are suspended in 30 ml of anhydrous DMF and mixed with 14 mM guanidine hydrochloride, under inert gas. The resulting mixture is stirred for 1 hour at 80° C. and, after cooling, filtered to remove any insoluble matter. The clear guanidine solution is added to the solution described above and stirred for 12 hours at ambient temperature. After the DMF has been distilled off under reduced pressure the residue is purified by chromatography on silica gel with a suitable solvent system. Treatment with ethereal hydrochloric acid or other pharmacologically acceptable acids converts the benzoylguanidines into the corresponding salts.

The following compounds may be obtained using this standard procedure:

EXAMPLE 1

Melting point: >250° C.

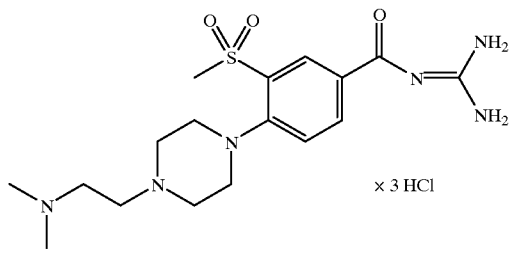

EXAMPLE 2

Melting point: 220–222° C. (decomp.)

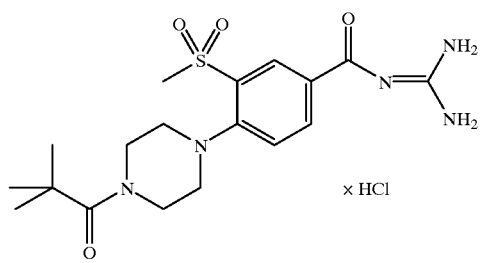

EXAMPLE 3

Melting point: 175–177° C. (decomp.)

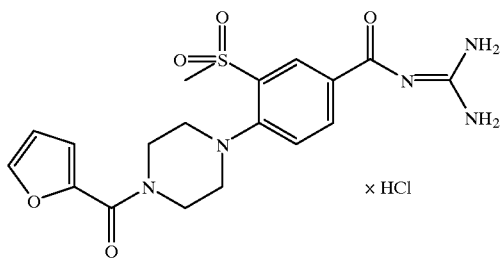

EXAMPLE 4

Melting point: >250° C.

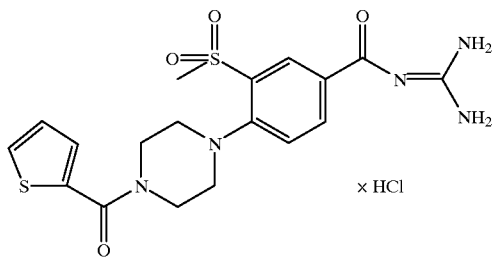

EXAMPLE 5

Melting point: 207–210° C. (decomp.)

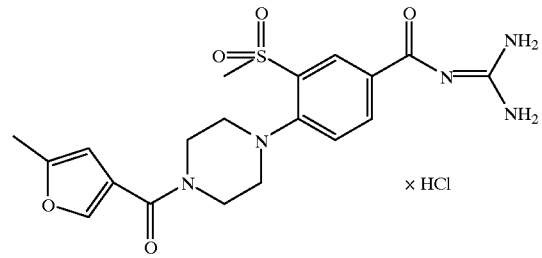

EXAMPLE 6

Melting point: 170–173° C.

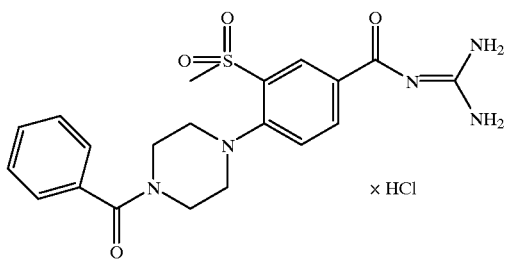

EXAMPLE 7

Melting point: 170° C. (decomp.)

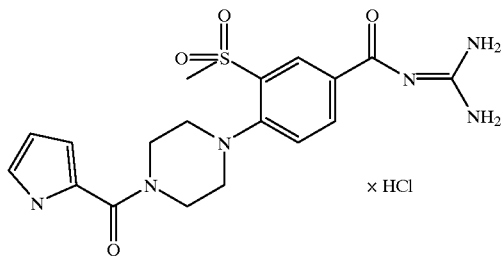

× HCl

EXAMPLE 8

Melting point: 243° C. (decomp.)

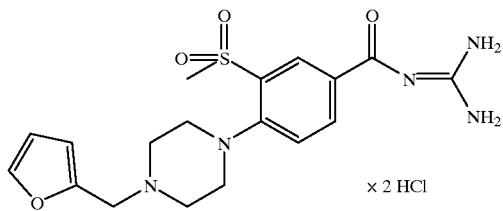

× 2 HCl

What is claimed is:

1. A benzoylguanidine derivative of Formula (IA)

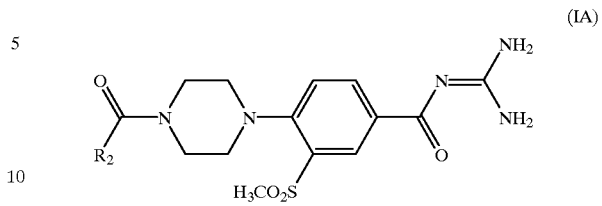

(IA)

wherein $R_2$ is
  (i) a five-membered ring having one hetero atom selected from the group consisting of O, N or S, which five-membered ring may be substituted by $C_{1-4}$ alkyl;
  (ii) a six-membered ring, which six-membered ring may have one hetero atom selected from N or O, which six-membered ring may be substituted by $C_{1-4}$ alkyl;
  (iii) naphthyl, which may be substituted by $C_{1-4}$ alkyl;
or a pharmaceutically acceptable acid addition salt thereof.

2. The benzoylguanidine derivative as recited in claim 1 wherein $R_2$ is furanyl.

3. The benzoylguanidine derivative as recited in claim 1 wherein $R_2$ is thiophenyl.

4. The benzoylguanidine derivative as recited in claim 1 wherein $R_2$ is pyrrolyl.

5. The benzoylguanidine derivative as recited in claim 1 wherein $R_2$ is phenyl.

6. The benzoylguanidine derivative as recited in claim 1 wherein $R_2$ is pyridinyl.

7. The benzoylguanidine derivative as recited in claim 1 wherein $R_2$ is naphthyl.

8. A pharmaceutical composition of matter comprising a benzoylguanidine derivative according to claim 1 together with a pharmaceutically acceptable excipient, diluent or carrier.

9. A method of treating a warm-blooded animal for ischemia which comprises administering to said animal a therapeutically effective amount of a benzoylguanidine derivative according to claim 1.

* * * * *